United States Patent
Okumura et al.

(10) Patent No.: US 7,421,062 B2
(45) Date of Patent: Sep. 2, 2008

(54) X-RAY CT APPARATUS AND DATA DETECTING METHOD OF X-RAY CT APPARATUS

(75) Inventors: Miwa Okumura, Utsunomiya (JP);
Satoru Nakanishi, Utsunomiya (JP);
Masaharu Tsuyuki, Nasushiobara (JP);
Yasuo Saito, Nasushiobara (JP)

(73) Assignees: Kabushiki Kaisha Toshiba, Tokyo (JP);
Toshiba Medical Systems Corporation, Otawara-shi (JP)

( * ) Notice: Subject to any disclaimer, the term of this patent is extended or adjusted under 35 U.S.C. 154(b) by 16 days.

(21) Appl. No.: 11/367,324

(22) Filed: Mar. 6, 2006

(65) Prior Publication Data
US 2006/0210014 A1     Sep. 21, 2006

(30) Foreign Application Priority Data
Mar. 7, 2005     (JP) .......................... P2005-061911

(51) Int. Cl.
H05G 1/58     (2006.01)
G01N 23/083     (2006.01)
(52) U.S. Cl. .............................. 378/116; 378/9; 378/19
(58) Field of Classification Search ................ 378/9, 378/19, 116
See application file for complete search history.

(56) References Cited

U.S. PATENT DOCUMENTS

| | | | | |
|---|---|---|---|---|
| 4,150,293 | A | 4/1979 | Franke | |
| 4,991,190 | A * | 2/1991 | Mori | 378/9 |
| 5,966,422 | A | 10/1999 | Dafni et al. | |
| 6,198,790 | B1 * | 3/2001 | Pflaum | 378/9 |
| 6,421,412 | B1 * | 7/2002 | Hsieh et al. | 378/9 |
| 7,016,455 | B2 * | 3/2006 | Bruder et al. | 378/9 |
| 7,039,153 | B2 * | 5/2006 | Bruder et al. | 378/9 |
| 7,062,006 | B1 * | 6/2006 | Pelc et al. | 378/9 |
| 7,194,061 | B2 * | 3/2007 | Fujita | 378/9 |
| 7,197,106 | B2 * | 3/2007 | Hartung et al. | 378/19 |
| 2004/0213371 | A1 | 10/2004 | Bruder et al. | |
| 2005/0089134 | A1 | 4/2005 | Bruder et al. | |

FOREIGN PATENT DOCUMENTS

| | | |
|---|---|---|
| JP | 2-52640 | 2/1990 |
| JP | 2004-223255 | 8/2004 |
| WO | WO 2005/004722 A2 | 1/2005 |

* cited by examiner

*Primary Examiner*—Edward J. Glick
*Assistant Examiner*—Thomas R Artman
(74) *Attorney, Agent, or Firm*—Oblon, Spivak, McClelland, Maier & Neustadt, P.C.

(57) ABSTRACT

An X-ray CT apparatus comprises three X-ray generating units, three groups of detecting elements and a reconstructing unit. The three X-ray generating units are arranged so as to make an angle formed by a first X-ray exposure direction and a second X-ray exposure direction on a rotational plane thereof be a same angle as that formed by the second X-ray exposure direction and a third X-ray exposure direction on the rotational plane, the same angle being smaller than 120 degree. The three groups of detecting elements are arranged opposite to the three X-ray generating units respectively so as to make a field of view formed in a center wider than two side fields of view. The reconstructing unit is configured to reconstruct an image using detection data detected by at least desired one of the three groups of the detecting elements.

20 Claims, 7 Drawing Sheets

X-RAY CT APPARATUS AND DATA DETECTING METHOD OF X-RAY CT APPARATUS

BACKGROUND OF THE INVENTION

1. Field of the Invention

The present invention relates to an X-ray CT (computed tomography) apparatus and a data detecting method of X-ray CT apparatus reconstructing a diagnostic image of an object using X-ray detection data acquired by exposing an X-ray to the object, and more particularly, to an X-ray CT apparatus and a data detecting method of X-ray CT apparatus having a plurality of tubes.

2. Description of the Related Art

An X-ray CT apparatus reconstructs a diagnostic image of an object by applying an X-ray from an X-ray tube to the object, acquiring X-ray detection data by an X-ray detector, and subjecting the acquired data to image reconstruction processing. Half reconstruction is one method for reconstructing a diagnostic image with the X-ray CT apparatus. In contrast to normal image reconstruction processing that reconstructs a diagnostic image by detecting data on an object over a range of 360°, half reconstruction reconstructs a diagnostic image by generating one image on the basis of projection data for an angle less than 360° (in general, projection data for the sum of 180° and the fan angle).

Half reconstruction is frequently used to obtain an image of a part, such as the heart, which moves locally, because of its capabilities of reconstructing an image from projection data for a narrow angle range and obtaining an image with high time resolution. In particular, when an image of the heart is obtained by half reconstruction using X-ray detection data for an angle less than 360° acquired in synchronization with an electrocardiogram (ECG), the influence of the heartbeats on the image can be reduced.

Figure 10:
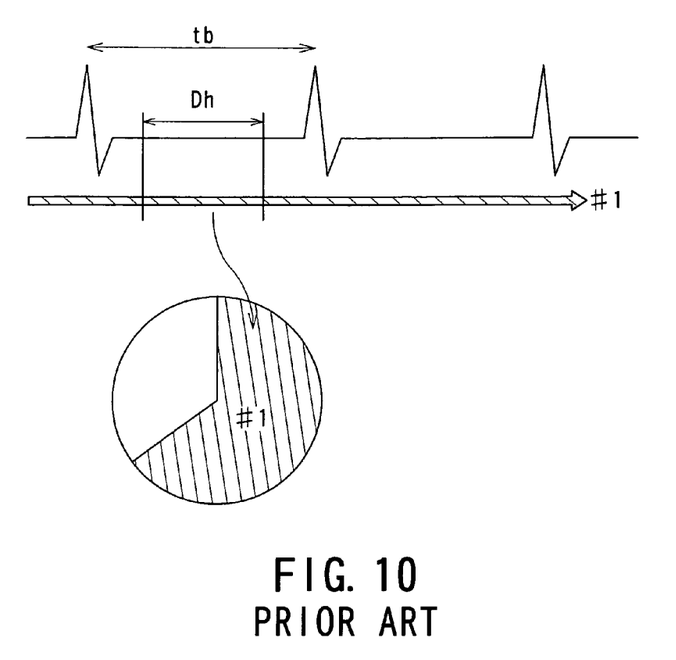
FIG. 10 is a conceptual diagram explaining the method for acquiring data for half reconstruction in synchronization with an electrocardiogram by the conventional X-ray CT apparatus.

FIG. 10 is a conceptual diagram explaining the method for acquiring data for half reconstruction in synchronization with an electrocardiogram by the conventional X-ray CT apparatus.

As shown in FIG. 10, an X-ray is applied from a tube #1 to an object, and half data Dh is acquired by an X-ray detector during the heartbeats shown in an ECG signal. The angle range of the half data Dh in FIG. 10 is set in the range of approximately 210° to 240°, for example, at 240°.

When the number of heartbeats per minute is 120 bpm, the length tb of one heartbeat is 0.5 sec, and therefore, high corresponding time resolution is required in order to acquire data within one heart beat. In normal cases, however, it is often difficult to sufficiently acquire half data within one heartbeat. Accordingly, a method of acquiring half data in divided segments within a plurality of heartbeats has been proposed.

Figure 11:
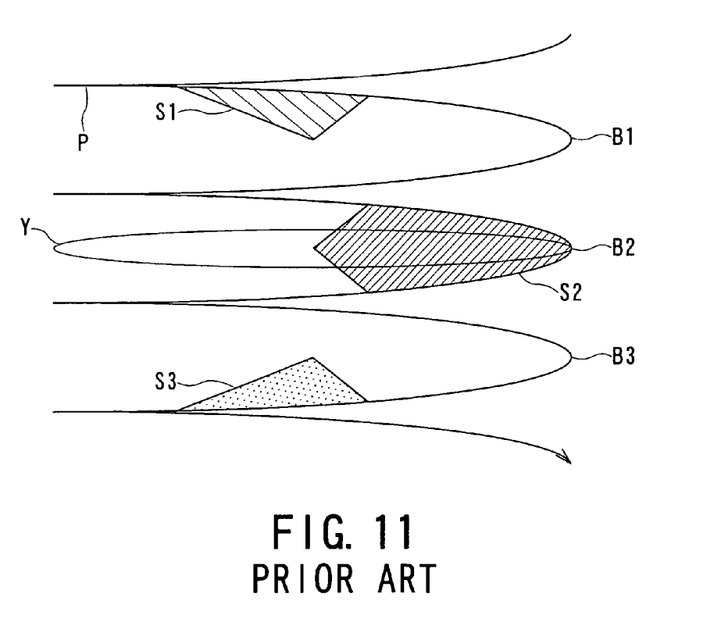
FIG. 11 is a conceptual diagram explaining the method for acquiring data for half reconstruction from divided segments in synchronization with an electrocardiogram by the conventional X-ray CT apparatus.

FIG. 11 is a conceptual diagram explaining the method for acquiring data for half reconstruction from divided segments in synchronization with an electrocardiogram by the conventional X-ray CT apparatus.

In the proposed method, while a tube is helically moved around an object, as shown by a tube locus p in FIG. 11, a first segment S1 of half data is acquired within a first heartbeat B1, and second and third segments S2 and S3 of the half data are acquired within second and third heartbeats B2 and B3 respectively. By data acquisition within three heartbeats, half data for approximately 240° on a reconstruction plane Y can be obtained.

On the other hand, a multi-tube X-ray CT apparatus have been proposed as an attempt to increase the time resolution. In the multi-tube X-ray CT apparatus, X-rays are emitted from a plurality of tubes to an object, and are detected by X-ray detectors arranged opposite to the corresponding tubes.

One of the multi-tube X-ray CT apparatuses is a three-tube X-ray CT apparatus including three tubes. In the proposed three-tube X-ray CT apparatus, three pairs of a tube and a detector are equally spaced 120° apart (see, for example, Japanese Patent Application (Laid-Open) No. H5-168616 or Japanese Patent Application (Laid-Open) No. 2001-346791). The three-tube X-ray CT apparatus enables 360° data to be acquired by rotating each pair 120°. For this reason, ideally, it is expected to acquire data in one third of the time taken for an X-ray CT apparatus including only one tube to acquire data.

Figure 12:
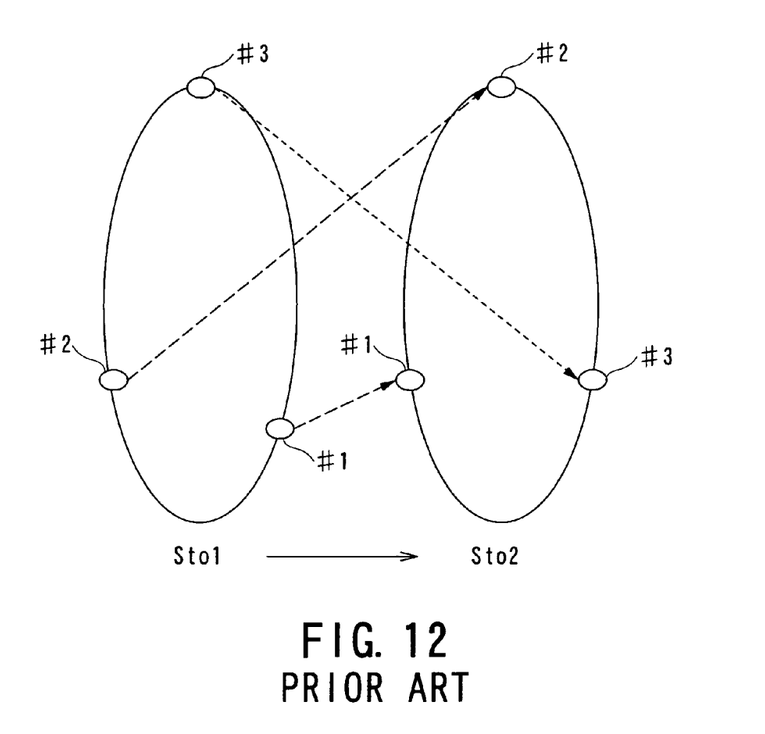
FIG. 12 is a conceptual diagram explaining the method for acquiring data by the conventional proposed three-tube X-ray CT apparatus.

FIG. 12 is a conceptual diagram explaining the method for acquiring data by the conventional proposed three-tube X-ray CT apparatus.

When three tubes #1, #2, and #3 are equally spaced 120° apart in a state St01 in FIG. 12, 360° data can be acquired by rotating the tubes #1, #2, and #3 120° into a state St02.

Therefore, when rotation speed of the tubes is 0.3 sec/rot, the time needed to acquire 360° data is 120/360×0.3=0.1 (sec), which is one third of the time taken when one tube is used.

Figure 13:
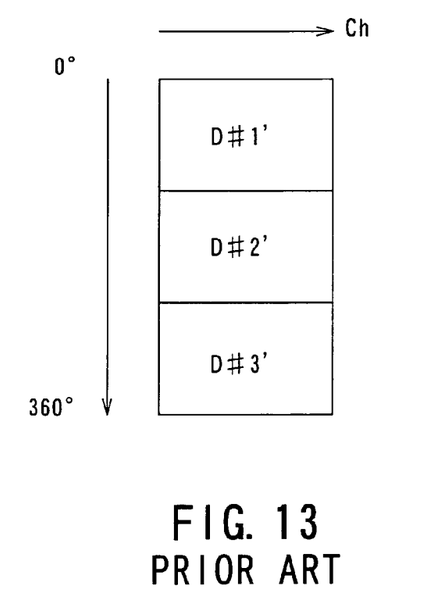
FIG. 13 is a conceptual diagram showing data acquired by the conventional proposed three-tube X-ray CT apparatus.

FIG. 13 is a conceptual diagram showing data acquired by the conventional proposed three-tube X-ray CT apparatus.

In FIG. 13, the ordinate indicates the data acquisition range expressed as the angle of application of X-rays to an object, and the abscissa indicates the used channels (Ch) of the X-ray detectors. As shown in FIG. 13, X-ray detectors #1', #2', and #3' opposing the three corresponding tubes #1, #2, and #3 acquire different data for each 120°. The X-ray detectors #1', #2', and #3' are equivalent in terms of the number of channels of detecting elements provided therein, and X-rays are detected in all the channels.

As a result, the equivalent number of data of 120° data D#1', D#2' and D#3' according to the number of the channels is acquired by the X-ray detectors #11, #21 and #3' respectively, as shown in FIG. 13. That is, 360° data that is proportional to the number of the channels is acquired by the three-tube X-ray CT apparatus.

Such a multi-tube X-ray CT apparatus is considered effective for high-speed scanning from a viewpoint of time resolution.

In the half reconstruction technology, enhancement of the time resolution is important, as described above. However, when half reconstruction is performed by a conventional one-tube X-ray CT apparatus, the time resolution is insufficient, and as a result, it is sometimes difficult to acquire necessary data within one heartbeat. For this reason, data is acquired in segments over a plurality of heartbeats.

Accordingly, the use of a multi-tube X-ray CT apparatus for such data acquisition that requires high time resolution is expected. However, when an image of a local part, such as the heart, is obtained with a multi-tube X-ray CT apparatus including equally spaced tubes, half reconstruction is not used, but full reconstruction is performed to acquire angularly continuous data on imaging.

In the multi-tube X-ray CT apparatus including equally spaced tubes, the tubes need not be rotated 360° because of the number of tubes, and this makes the time resolution higher than when full reconstruction is performed with a one-tube X-ray CT apparatus. On the other hand, it is difficult to use half reconstruction. For this reason, there is a demand to further increase the time resolution on imaging of a local part.

Further, when a plurality of pairs of a tube and an X-ray detector are provided to ensure a sufficient FOV (field of view) on the multi-tube X-ray CT apparatus, the manufacturing cost increases. In general, high time resolution is particularly required mainly in a case in which the FOV is narrow and an image of a local part, such as the heart, is obtained. Therefore, the time resolution is also expected to be increased with a simpler configuration.

SUMMARY OF THE INVENTION

The present invention has been made in light of the conventional situations, and it is an object of the present invention to provide an X-ray CT apparatus and a data detecting method of X-ray CT apparatus which can image with time resolution and FOV according to a purpose by exposing X-rays from a plurality of tubes to an object.

Furthermore, it is another object of the present invention to provide an X-ray CT apparatus and a data detecting method of X-ray CT apparatus which can image with locally improved time resolution on half reconstruction by exposing X-rays from a plurality of tubes to an object.

The present invention provides an X-ray CT apparatus comprising: three X-ray generating units arranged so as to make an angle formed by a first X-ray exposure direction and a second X-ray exposure direction on a rotational plane thereof be a same angle as that formed by the second X-ray exposure direction and a third X-ray exposure direction on the rotational plane, the same angle being smaller than 120 degree; three groups of detecting elements arranged opposite to the three X-ray generating units respectively so as to make a field of view formed in a center wider than two side fields of view; and a reconstructing unit configured to reconstruct an image using detection data detected by at least desired one of the three groups of the detecting elements, in an aspect to achieve the object.

The present invention also provides an X-ray CT apparatus comprising: X-ray generating units arranged so as to expose X-rays in mutually different rotational radius directions and make angles formed by adjacent two X-ray exposure directions unequal mutually; groups of detecting elements arranged opposite to the X-ray generating units respectively; a supporting member supporting at least two of the groups in common; and a reconstructing unit configured to reconstruct an image using detection data from at least desired one of the groups, in an aspect to achieve the object.

The present invention also provides an X-ray CT apparatus comprising: a first X-ray generating unit configured to expose an X-ray in a first exposure direction; a second X-ray generating unit configured to expose an X-ray in a second exposure direction which is different from the first exposure direction on a rotational plane thereof; a first group of detecting elements of which at least one of a size and a pitch between adjacent detecting elements of some detecting elements is different from that of other detecting elements, the first group being opposite to the first X-ray generating unit; a second group of detecting elements opposite to the second X-ray generating unit; and a reconstructing unit configured to reconstruct an image using data detected by at least one of the first group and the second group, in an aspect to achieve the object.

The present invention also provides a data detecting method of X-ray CT apparatus comprising steps of: exposing an X-ray from at least one of three X-ray generating units arranged in positions so as to make an angle formed by a first X-ray exposure direction and a second X-ray exposure direction on a rotational plane thereof be a same angle as that formed by the second X-ray exposure direction and a third X-ray exposure direction on the rotational plane, the same angle being smaller than 120 degree; detecting an exposed X-ray as detection data using at least one of three groups of detecting elements arranged opposite to the three X-ray generating units respectively so as to make a field of view formed in a center wider than two side fields of view; and reconstructing an image using the detection data, in an aspect to achieve the object.

The present invention also provides a data detecting method of X-ray CT apparatus comprising steps of: exposing an X-ray from at least one of X-ray generating units arranged so as to expose X-rays in mutually different rotational radius directions and make angles formed by adjacent two X-ray exposure directions unequal mutually; detecting an exposed X-ray as detection data by at least one of groups of detecting elements arranged opposite to the X-ray generating units respectively, at least two of the groups being supported by a common supporting member; and reconstructing an image using the detection data, in an aspect to achieve the object.

The present invention also provides a data detecting method of X-ray CT apparatus comprising steps of: exposing an X-ray from at least one of a first X-ray generating unit for exposing an X-ray in a first exposure direction and a second X-ray generating unit for exposing an X-ray in a second exposure direction which is different from the first exposure direction on a rotational plane thereof; detecting an exposed X-ray as detection data by at least one of a first group of detecting elements of which at least one of a size and a pitch between adjacent detecting elements of some detecting elements is different from that of other detecting elements and a second group of detecting elements opposite to the second X-ray generating unit, the first group being opposite to the first X-ray generating unit; and reconstructing an image using the detection data, in an aspect to achieve the object.

The X-ray CT apparatus and the data detecting method of X-ray CT apparatus as described above make it possible to image with time resolution and FOV according to a purpose by exposing X-rays from a plurality of tubes to an object.

Furthermore, it is possible to image with locally improved time resolution on half reconstruction by exposing X-rays from a plurality of tubes to an object.

DESCRIPTION OF THE PREFERRED EMBODIMENTS

An X-ray CT apparatus and a data detecting method of X-ray CT apparatus according to embodiments of the present invention will be described with reference to the accompanying drawings.

Figure 1:
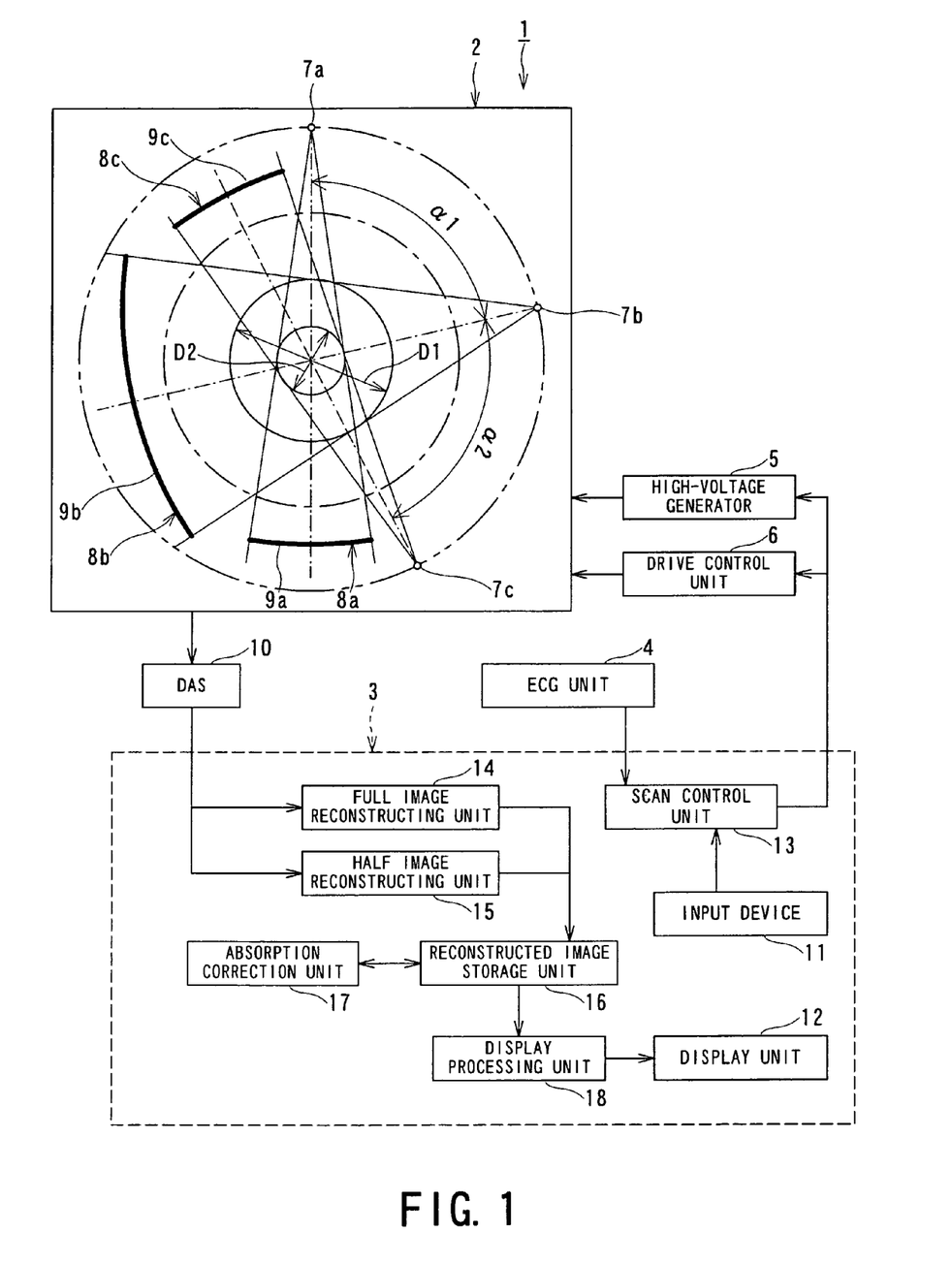
FIG. 1 is a functional block diagram showing an X-ray CT apparatus according to a first embodiment of the present invention.

FIG. 1 is a functional block diagram showing an X-ray CT apparatus according to a first embodiment of the present invention.

An X-ray CT apparatus 1 includes a gantry 2, a computer 3, and an ECG unit 4. The gantry 2 includes a high-voltage generator 5, a drive control unit 6, a plurality of X-ray tubes, such as three tubes 7a, 7b, and 7c, for emitting X-rays from focus portions (X-ray emitting portions), X-ray detectors 9a, 9b, and 9c arranged opposed to the corresponding tubes 7a, 7b, and 7c to form pairs 8a, 8b, and 8c, and a data acquisition system (DAS) 10.

The tubes 7a, 7b, and 7c and the X-ray detectors 9a, 9b, and 9c are arranged on a common rotating member (not shown), and are rotated on the same plane by rotating the rotating member. The rotating member is rotatably supported on a gantry fixing unit by a bearing.

The high-voltage generator 5 provided in the gantry 2 applies a high-voltage to k-ray tubes constituted by the tubes 7a, 7b, and 7c so that the tubes 7a, 7b, and 7c emit X-rays to an object. The drive control unit 6 rotates the rotating member to rotate the tubes 7a, 7b, and 7c and the X-ray detectors 9a, 9b, and 9c opposed to the tubes.

That is, in the X-ray CT apparatus 1, the pairs 8a, 8b, and 8c respectively formed by the tubes 7a, 7b, and 7c and the X-ray detectors 9a, 9b, and 9c are rotated by the driving control unit 6, and a high voltage is applied from the high-voltage generator 5 to the tubes 7a, 7b, and 7c. By the application of the high voltage, X-rays are emitted from the tubes 7a, 7b, and 7c to an object, and are then detected by the X-ray detectors 9a, 9b, and 9c opposed to the corresponding tubes 7a, 7b, and 7c. X-ray detected data obtained by the X-ray detectors 9a, 9b, and 9c are given to the DAS 10 so as to be converted into digital raw data.

The pairs 8a, 8b, and 8c of the tubes 7a, 7b, and 7c and the X-ray detectors 9a, 9b, and 9c are unequally spaced so that data acquisition can be properly performed by image reconstruction, preferably, half reconstruction, so that the pairs 8a, 8b, and 8c cover at least the required ranges, and so that one, two, or all of the angles formed between the adjoining pairs 8a, 8b, and 8c in the direction of application of the X-rays are different. Preferably, the pairs 8a, 8b, and 8c are arranged at the positions corresponding to the angles obtained by equally dividing the angle range necessary for data acquisition by half reconstruction. That is, it is preferable that the tubes 7a, 7b, and 7c be arranged at the positions corresponding to the angles obtained by equally dividing an appropriate angle range for half reconstruction and that the X-ray detectors 9a, 9b, and 9c be arranged opposed to the corresponding tubes 7a, 7b, and 7c respectively.

For example, when the appropriate angle for data acquisition by half reconstruction is 240° and three tubes 7 are provided, as shown in FIG. 1, the other pairs 8a and 8c are arranged on both sides of the pair 8b serving as the reference so as to cross the pair 8b at $\alpha 1 = \alpha 2 = 80°$ which is one third of 240°. The reference pair is not limited to the center pair 8b, and may be any of the pairs 8a, 8b, and 8c. Further, the angles $\alpha 1$ and $\alpha 2$ shown in FIG. 1 may be different from each other.

While it is, in actuality, possible to acquire data for a range enlarged by the fan beam angle of the X-ray, herein, consideration is given only to the positional relationship among the center lines of the pairs of 8a, 8b, and 8c for simple explanation.

The X-ray detectors 9a, 9b, and 9c are two-dimensional detectors, and each include a plurality of rows of detecting elements for a plurality of channels arranged along the direction of the body axis (direction perpendicular to the plane of FIG. 1). While each of the X-ray detectors 9a, 9b, and 9c includes a plurality of detecting elements, the X-ray detector 9 in at least one pair 8 includes a number of detecting elements corresponding to a sufficient number of channels to cover a wide FOV needed to obtain an image of the entire cross section of the object by full reconstruction or half reconstruction. On the other hand, the X-ray detector 9 in the other pair 8 includes a number of detecting elements corresponding to a sufficient number of channels to cover an appropriate local FOV (narrower than the above-described wide FOV) for imaging by half reconstruction. In this embodiment, the local FOV has a size that is proper for imaging of the heart.

For example, as shown in FIG. 1, the X-ray detector 9b of the center pair 8b includes a number of detecting elements corresponding to approximately 1000 channels that sufficiently cover a wide FOV having a diameter D1 of approximately 500 mm suited for imaging by full reconstruction or half reconstruction. Each of the X-ray detectors 9a and 9b in the side pairs 8a and 8c includes a number of detecting elements corresponding to approximately 500 channels that sufficiently cover a local FOV having a diameter D2 of approximately 200 mm suited for imaging by half reconstruction.

The computer 3 includes an input device 11, a display unit 12, a scan control unit 13, a full image reconstructing unit 14 as an example of a second image reconstructing unit, a half image reconstructing unit 15 as an example of a first image reconstructing unit, a reconstructed image storage unit 16, an absorption correction unit 17, and a display processing unit 18. All or some of the above-described elements can be constructed with circuits or by reading a data processing program into an operation device (not shown).

The ECG unit 4 obtains an ECG signal of the object, and sends the ECG signal to the scan control unit 13.

The scan control unit 13 is triggered by the ECG signal received from the ECG unit 4, and outputs a control signal to the high-voltage generator 5 to execute ECG-synchronized scanning. Further, the scan control unit 13 determines the imaging range and whether imaging is to be performed by full reconstruction or half reconstruction in accordance with an instruction inputted from the input device 11. Depending on the determined reconstruction method, the scan control unit 13 sends control signals to the high-voltage generator 5 and the drive control unit 6 so that it can control which of the tubes 7a, 7b, and 7c emit X-rays, the emission timing, and the rotation angle of the tubes 7a, 7b, and 7c and the X-ray detectors 9a, 9b, and 9c.

Under the control of the scan control unit 13, data acquisition is performed with the X-ray detector 9b including the detecting elements that cover a wide FOV on imaging for a wide range, and with a plurality of X-ray detectors 9 including the detecting elements which cover a local FOV on imaging for a local range by half reconstruction, preferably, all the X-ray detectors 9a, 9b, and 9c.

In other words, the scan control unit 13 switches between imaging modes on the basis of a command from the input device 11. It is possible to set, as the imaging modes, a first imaging mode in which imaging is performed by full reconstruction over a wide FOV only with the center large X-ray detector 9b, as described above, and a second imaging mode in which imaging is performed by half reconstruction over a local FOV with all the X-ray detectors 9a, 9b, and 9c.

The first imaging mode can cover a wide FOV. While the FOV is local in the second imaging mode, the number of detecting elements used for data acquisition is large in the rotating direction of the X-ray detectors 9a, 9b, and 9c, and therefore, the time necessary for data acquisition can be made shorter than in the first imaging mode. This can achieve a high time resolution for a local FOV. For this reason, the second imaging mode is suitable for, for example, scanning the heart. An imaging mode may be set in which reconstruction other than half reconstruction is performed for data acquired from a local FOV.

Further, an arbitrary imaging condition can be set as an imaging mode. Other imaging modes that are effective when data acquisition is performed with the three X-ray detectors 9a, 9b, and 9c, as shown in FIG. 1, are, for example, a third imaging mode in which the two X-ray detectors 9a and 9b, that is, the large X-ray detector 9b covering a wide FOV and one small X-ray detector 9a covering a local FOV are used and in which different energies (tube voltages) are applied to the X-ray detectors 9a and 9b, and a fourth imaging mode in which two small X-ray detectors 9a and 9c covering a local FOV are used and in which different energies (tube voltages) are applied to the X-ray detectors 9a and 9c.

In the third imaging mode, two images having different contrasts can be obtained by using data from a wide FOV and data from a local FOV. By combining the two images, an image having contrast that is diagnostically useful can be obtained. In the fourth imaging mode, the crossing angle formed by the paths of X-rays exposed from the two tubes 7a and 7c is larger than in the third imaging mode. For this reason, the fourth imaging mode can reduce the occurrence and influence of scattered rays.

In the third and fourth imaging modes, control information about the voltage to be generated and information about which of the tubes 7a, 7b, and 7c is to be used is sent from the scan control unit 13 to the high-voltage generator 5 in order to adjust the tube voltages to be applied to the X-ray detectors 9a and 9b or the X-ray detectors 9a and 9c.

The first and second imaging modes will be described below.

The full image reconstructing unit 14 obtains, from the DAS 10, raw data acquired from an FOV for full reconstruction, and reconstructs image data by subjecting the raw data to image reconstructing processing. The full image reconstructing unit 14 also writes the reconstructed image data in the reconstructed image storage unit 16 to be stored in it. That is, the full image reconstructing unit 14 reconstructs image data by full reconstruction using data detected by the detecting elements of the X-ray detector 9b that can acquire data from a FOV for full reconstruction wider than a local FOV for half reconstruction.

The half image reconstructing unit 15 obtains, from the DAS 10, raw data acquired from a local region for half reconstruction, and reconstructs local image data by subjecting the raw data to image reconstructing processing for half reconstruction. The half image reconstructing unit 15 also writes the reconstructed image data in the reconstructed image storage unit 16 to be stored in it.

The absorption correction unit 17 subjects the local image data, which is reconstructed by half reconstruction and is stored in the reconstructed image storage unit 16, to absorption correction using data acquired from the outside of the local region. That is, the absorption correction unit 17 makes absorption correction to the image data reconstructed by the half image reconstructing unit 15 by using data from outside the local region, of the data detected by the detecting elements of the X-ray detector 9b that can acquire data from the region wider than the local region.

The display processing unit 18 generates image signals by subjecting the image data stored in the reconstructed image storage unit 16 to display processing, and sends the generated image signals to the display unit 12 to display images.

The action and operation of the X-ray CT apparatus 1 will now be described. A description will be given of a case in which three pairs 8 are provided and in which two pairs 8a and 8c each covering a local FOV are arranged on either side of a center pair 8b covering a wide FOV so as to cross the center pair 8b at an angle of 80°, as shown in FIG. 1.

First, the input device 11 directs the scan control unit 13 to perform a wide-range imaging of an object by full reconstruction or local imaging of, for example, the heart by half reconstruction. For example, when the scan control unit 13 is directed to perform wide-range imaging of the object by full reconstruction, the center pair 8b is used for imaging.

That is, in synchronization with an ECG signal from the ECT unit 4, control signals are given from the scan control unit 13 to the high-voltage generator 5 and to the drive control unit 6. An X-ray is applied from the center tube 7b to an object (not shown), passes through the object, and is detected by the X-ray detector 9b that covers a wide FOV. The detected X-rays are converted into raw data by the DAS 10, which is then output to the full image reconstructing unit 14.

The full image reconstructing unit 14 generates image data by executing image reconstruction processing using only the raw data obtained via the X-ray detector 9b that covers the wide FOV. Therefore, wide-range image data is generated by the full image reconstructing unit 14. The generated image data is appropriately stored in the reconstructed image storage unit 16, and is then given as image signals from the display processing unit 18 to the display unit 12 so as to enable the image to be displayed.

For example, when the scan control unit 13 is directed to perform local imaging of the heart by half reconstruction over a data acquisition range of 240°, all the three pairs 8a, 8b, and 8c are used for imaging.

That is, X-rays are exposed from all the three tubes 7a, 7b, and 7c onto an object (not shown) in synchronization with an ECG signal from the ECG unit 4, pass through the object, and are detected by the center X-ray detector 9b covering the wide FOV and the two side X-ray detectors 9a and 9c covering the local FOV. In this case, while data acquisition ranges of the X-ray detectors 9a, 9b, and 9c may slightly overlap, they are different in substance.

Figure 2:
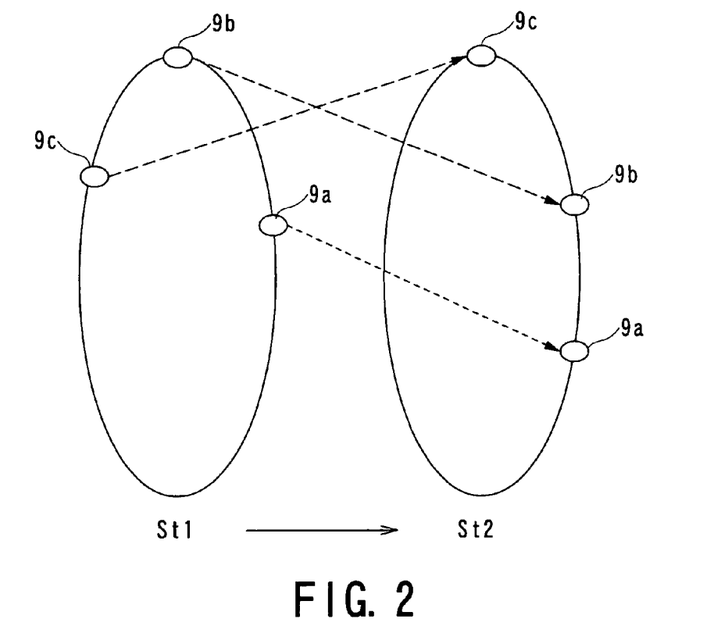
FIG. 2 is a diagram showing the changes of the positions of the X-ray detectors in the X-ray CT apparatus shown in FIG. 1 during detection of data for half reconstruction using the three X-ray detectors.

FIG. 2 is a diagram showing the changes of the positions of the X-ray detectors 9a, 9b, and 9c in the X-ray CT apparatus 1 shown in FIG. 1 during detection of data for half reconstruction using the three X-ray detectors 9a, 9b, and 9c.

Since the data acquisition ranges of the three X-ray detectors 9a, 9b, and 9c are different, when the total data acquisition range is 240°, necessary data can be acquired by rotating the X-ray detectors 9a, 9b, and 9c 80° from a state St1 to a St2, as shown in FIG. 2. That is, half image reconstruction can be performed by the multi-tube X-ray CT apparatus 1.

Figure 3:
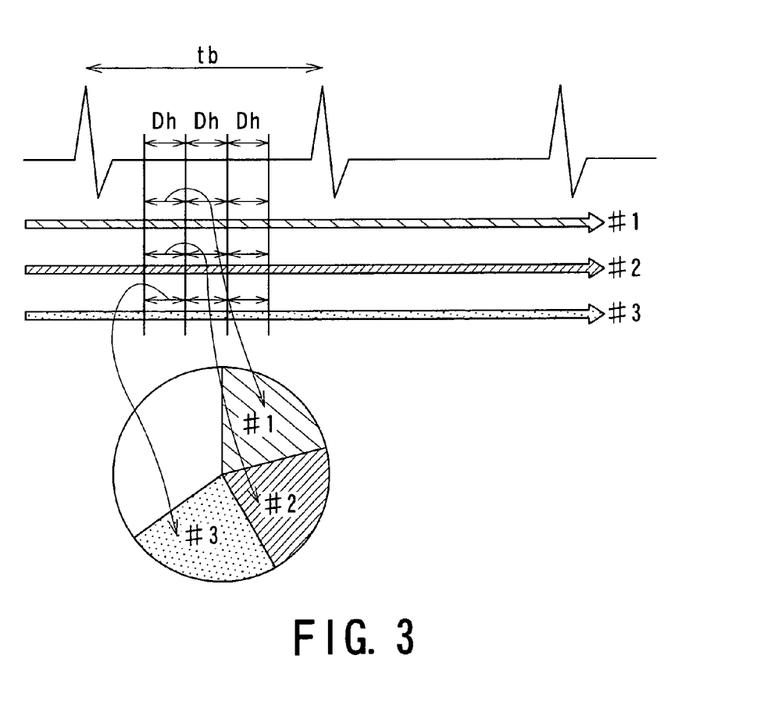
FIG. 3 is a conceptual diagram explaining the method for detecting data for half reconstruction using the three X-ray detectors in synchronization with an ECG signal by the X-ray CT apparatus shown in FIG. 1.
Figure 4:
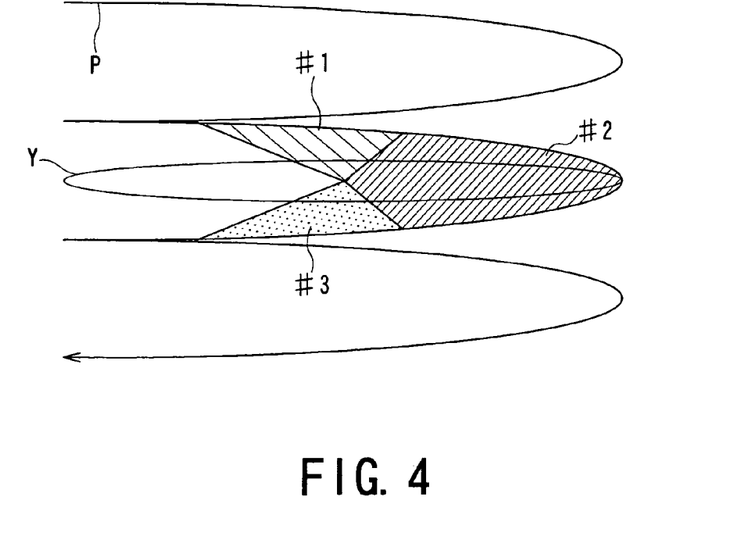
FIG. 4 is another conceptual diagram explaining the method for detecting data for half reconstruction using the three X-ray detectors in synchronization with an ECG signal by the X-ray CT apparatus shown in FIG. 1.

FIG. 3 is a conceptual diagram explaining the method for detecting data for half reconstruction using the three X-ray detectors 9a, 9b, and 9c in synchronization with an ECG signal by the X-ray CT apparatus 1 shown in FIG. 1. FIG. 4 is another conceptual diagram explaining the method for detecting data for half reconstruction using the three X-ray detectors 9a, 9b, and 9c in synchronization with an ECG signal by the X-ray CT apparatus 1 shown in FIG. 1.

As shown in FIG. 3, data for half reconstruction are simultaneously detected by the three X-ray detectors 9a, 9b, and 9c during the heartbeats shown in an ECG signal. That is, X-rays applied from the three tubes 7a, 7b, and 7c are simultaneously detected by the corresponding first (#1), second (#2), and third (#3) X-ray detectors 9a, 9b, and 9c, thereby acquiring half data Dh.

When the number of heartbeats per minute is 120 bpm, the length tb of one heartbeat is 0.5 sec. The time needed to rotate the tubes 7a, 7b, and 7c by 80° is 80/360×0.3≈0.07 (sec) when the rotation speed of the tubes 7a, 7b, and 7c is 0.3 sec/rot. That is, the time needed to perform data acquisition for 240° is 0.07 sec, and high time resolution with respect to the length of one heartbeat can be achieved.

For this reason, as shown by a tube locus p in FIG. 4, the tubes 7a, 7b, and 7c are helically moved around the object, and data for 240° in a reconstruction plane Y are simultaneously acquired from separate regions by the first (#1), second (#2), and third (#3) X-ray detectors 9a, 9b, and 9c within one heartbeat. Further, data acquisition can sometimes be performed a plurality of times during one heartbeat, as shown in FIG. 3. For example, data accuracy can be increased by acquiring data a plurality of times and averaging the data.

That is, as shown by a lower chart in FIG. 3, data for a 80° segment, of the 240° for half reconstruction, is acquired by the first (#1) X-ray detector 9a, data for another 80° segment is acquired by the second (#2) X-ray detector 9b, and data for the remaining 80° segment is acquired by the third (#3) X-ray detector 9c.

The X-ray detection data thus acquired by the X-ray detectors 9a, 9b, and 9c are converted into raw data by the DAS 10, are combined for half reconstruction, and are then outputted to the half image reconstructing unit 15.

Figure 5:
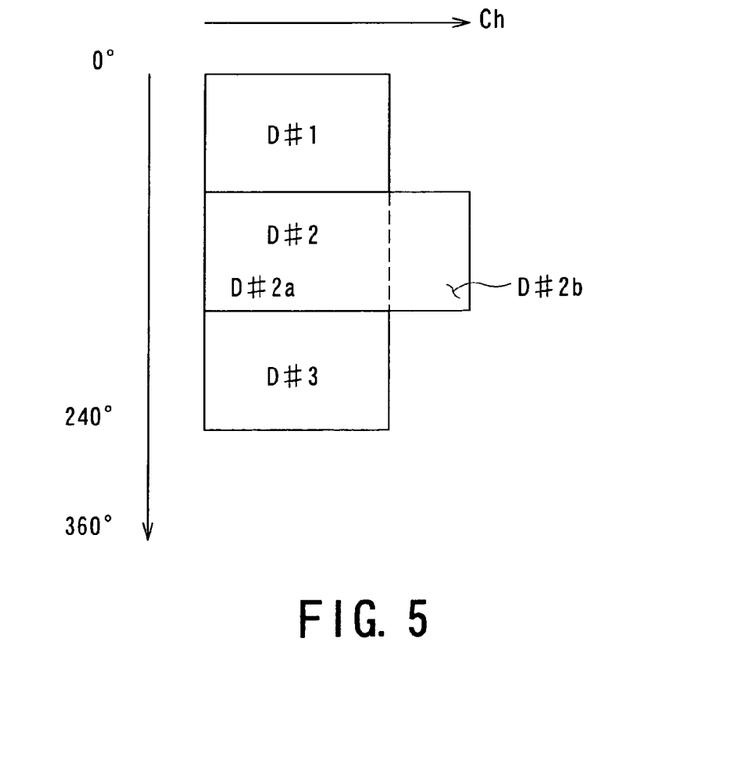
FIG. 5 is a conceptual diagram showing data for half reconstruction acquired by the three X-ray detectors of the X-ray CT apparatus shown in FIG. 1.

FIG. 5 is a conceptual diagram showing data for half reconstruction acquired by the three X-ray detectors 9a, 9b, and 9c of the X-ray CT apparatus 1 shown in FIG. 1.

In FIG. 5, the abscissa indicates the channel (Ch) to which the acquired data belong, and the ordinate indicates the data acquisition range expressed by the angle of application of the X-rays onto the object.

As shown in FIG. 5, data D#1, D#2, and D#3 for each 80° are respectively acquired by the first (#1), second (#2), and third (#3) X-ray detectors 9a, 9b, and 9c, and consequently, data for the total angle of 240° that is appropriate for half reconstruction can be obtained.

Since the first (#1) and third (#3) X-ray detectors 9a and 9c each include a number of detecting elements only corresponding to the number of channels that cover the local FOV, they acquire data D#1 and D#3 on fewer channels than those in case of the second (#2) X-ray detector 9b including a number of detecting elements corresponding to the channels that cover the wide FOV. In other words, data D#1 and D#3 acquired by the first (#1) and third (#3) X-ray detectors 9a and 9c are obtained only from the channels in the local FOV.

In contrast, data D#2 acquired by the second (#2) X-ray detector 9b can be divided into data D#2a from channels within the local FOV and data D#2b from channels within the wide FOV outside the local FOV.

Therefore, the half image reconstructing unit 15 reconstructs image data by using the data D#1, D#2a, and D#3 from the channels within the local FOV obtained by the first (#1), second (#2), and third (#3) X-ray detectors 9a, 9b, and 9c in an ECG-synchronized manner. The obtained local image data is appropriately stored in the reconstructed image storage unit 16. In this case, the data D#2b, which is acquired by the second (#2) X-ray detector 9b from the channels within the wide FOV outside the local FOV, can be added as additional information to the obtained image data for the purpose of absorption correction which will be described below.

As required, the absorption correction unit 17 subjects the local image data, which is reconstructed by half reconstruction by the half image reconstructing unit 15 and stored in the reconstructed image storage unit 16, to absorption correction using the data D#2b, serving as the additional information, obtained from the outside the local region.

That is, when the local image data is, for example, image data on the heart, it is expressed as a CT value of the heart. However, it is sometimes clinically important to find a CT value of the heart as a relative value with respect to a CT value of air outside the object. Accordingly, in absorption correction, a CT value of the heart can be found as a relative value with respect to a CT value of air on the basis of the difference between a CT value of a tissue near the heart and a CT value of air when the difference can be obtained.

In this case, the data D#2b acquired as the additional information from the outside of the local region can be used for absorption correction.

Further, the image data is stored again in the reconstructed image storage unit 16 after absorption correction, and is given as image signals from the display processing unit 18 to the display unit 12 so as to enable the image to be displayed.

In the above-described X-ray CT apparatus 1, an image can be obtained with a time resolution and an FOV, which fit the required purpose, by switching between half reconstruction and full reconstruction. In particular, imaging can be performed with a time resolution locally increased by half reconstruction. More specifically, half reconstruction can be performed with a time resolution of 50 to 60 msec.

Especially, arranging the three X-ray detectors 9a, 9b and 9c to line symmetry on the rotational plane so as to be near as much as possible mutually and setting the FOV of the center X-ray detector 9b wider than that of the two side X-ray detectors 9a and 9c as shown in FIG. 1 make it possible to arrange more detecting elements without interference to improve time resolution as well as facilitate processing of data by symmetry property. In addition, setting the distances between the adjacent X-ray detectors 9a, 9b and 9c shorter gives a wider size of FOV which can acquire data with high time resolution.

A modification of the X-ray CT apparatus 1 will now be described.

Figure 6:
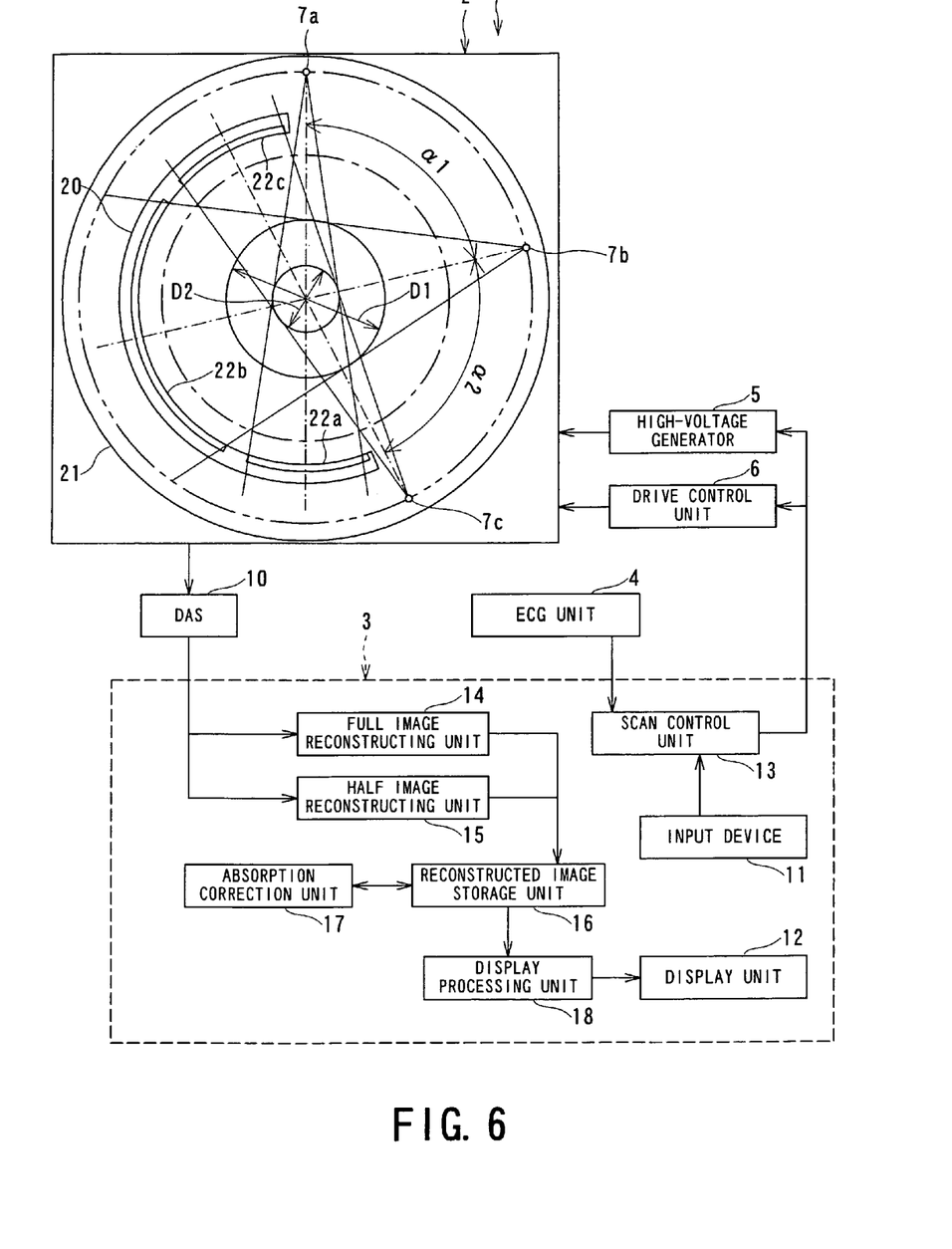
FIG. 6 is a functional block diagram showing a modified example of the X-ray CT apparatus shown in FIG. 1.

FIG. 6 is a functional block diagram showing a modified example of the X-ray CT apparatus 1 shown in FIG. 1.

As shown in FIG. 6, X-ray detectors do not always need to be physically separate as long as they can detect X-rays exposed from a plurality of different directions. That is, a plurality of or a single common detector support frame 20 may be provided inside a rotating frame 21, and a plurality of groups of detecting elements can be provided as detector units 22a, 22b, and 22c on the detector support frame 20. The rotating frame 21 is typically cast in metal such as aluminum. For this reason, the detector support frame 20 can also be integral cast in metal, such as aluminum, as a part of the rotating frame 21. In the modification shown in FIG. 6, three detector units 22a, 22b, and 22c are provided on the single detector support frame 20, the center detector unit 22b can cover a wide FOV, and the two side detector units 22a and 22c can cover a local FOV, for example.

When these detector units 22a, 22b, and 22c are used, positional interference among the X-ray detectors 9a, 9b, and 9c shown in FIG. 1 does not occur. For this reason, the distances between the detector units 22a, 22b, and 22c, that is, between the groups of detecting elements can be reduced. Consequently, a local FOV that allows high time resolution can be enlarged. Moreover, the positioning accuracy of the detecting elements can be increased. In contrast, when a plurality of X-ray detectors 9a, 9b, and 9c are separately provided, as shown in FIG. 1, production is facilitated.

The configuration and structures of the above-described X-ray CT apparatus 1 may be simplified. For example, when a plurality of X-ray detectors 9 are equally spaced, and are made different only in the number of channels of groups of detecting elements, that is, in the size of the FOV which the detectors can cover, the manufacturing cost of the X-ray detectors 9 can be decreased while the time resolution of the multi-tube X-ray CT apparatus can be obtained. Conversely, when X-ray detectors 9 that can cover the same FOV are unequally spaced at appropriate positions for half reconstruction, the manufacturing cost of the X-ray detectors 9 is increased, but it can be expected to provide an apparatus specialized in imaging with high time resolution over a wider FOV and half reconstruction of a local image.

Figure 7:
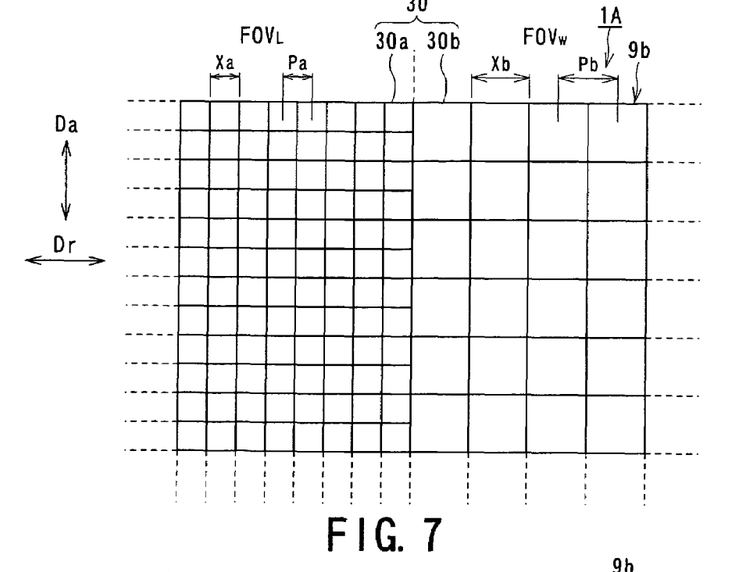
FIG. 7 is a diagram showing a structure of an X-ray detector included in an X-ray CT apparatus according to a second embodiment of the present invention.

FIG. 7 is a diagram showing a structure of an X-ray detector included in an X-ray CT apparatus according to a second embodiment of the present invention.

An X-ray CT apparatus 1A shown in FIG. 7 is different from the X-ray CT apparatus 1 shown in FIG. 1 in terms of the sizes and arrangements (center distances) of detecting elements 30 provided in at least one of a plurality of X-ray detectors 9a, 9b, and 9c, practically, in the X-ray detector 9b that covers a wide FOV. Since other structures and operations are substantially the same as those employed in the X-ray CT apparatus 1 shown in FIG. 1, only the X-ray detector 9b is shown. The same structures are denoted by the same reference numerals, and descriptions thereof are omitted.

In the X-ray detector 9b of the X-ray CT apparatus 1A, a plurality of detecting elements 30 are two-dimensionally arrayed in the rotating direction Dr of the X-ray detector 9b and in the direction Da of the rotation axis thereof. Some of the detecting elements 30 have a size different from that of the other detecting elements 30. Further, the center distance (pitch) between some adjoining detecting elements 30 is different from that of the other adjoining detecting elements 30. At least one of the size and the pitch may be different between the detecting elements.

In practice, it is preferable that the pitch Pa between the adjoining detecting elements 30a having a small size Xa be short according to the size Xa and that the pitch Pb between the adjoining detecting elements 30b having a large size Xb be long according to the size Xb, as shown in FIG. 7. In the example shown in FIG. 7, the size Xa of some detecting elements 30a is half the size Xb of the other detecting elements 30b, and the pitch Pa between the small detecting elements 30a having the half size Xa is half the pitch Pb between the detecting elements 30b having the large size Xb.

While the sizes Xa and Xb of the detecting elements 30a and 30b and the pitches Pa and Pb between the detecting elements 30a and 30b are different in the two-dimensional directions in the X-ray detector 9b shown in FIG. 7, they may be different only in the rotating direction Dr of the X-ray detector 9b.

When the size of some detecting elements 30 is changed in the X-ray detector 9b in this way, sensitivity of the large-sized detecting elements 30 increases to reduce noise, depending on the size X thereof. Conversely, spatial resolution and time resolution of the small-sized detecting elements 30 can be increased depending on the size thereof. That is, sections that are different in sensitivity, time resolution and spatial resolution can be formed on the single X-ray detector 9b.

In contrast, when the pitch P between some detecting elements 30 is changed, noise is reduced in a section of the X-ray detector 9b in which the pitch P is long, depending on the pitch P. Moreover, since the structure is simplified, the manufacturing cost can be reduced. Conversely, the time resolution and spatial resolution can be increased in a section of the X-ray detector 9b in which the pitch P is short, depending on the pitch P. That is, when the pitch P between some detecting elements 30 is changed, sections that are different in time resolution and spatial resolution can also be formed on the single X-ray detector 9b.

Since a section of the X-ray detector 9b for detecting data from the local $FOV_L$ is required to have higher time resolution and higher spatial resolution, detecting elements 30 having a smaller size X are preferably arranged in the section at a shorter pitch P. Conversely, in order to simplify the structure of a section of the X-ray detector 9b for detecting data only from a wide $FOV_W$, detecting elements 30 having a size X such as to detect data necessary for at least image reconstruction are preferably arranged in the section at the required pitch P.

Accordingly, when the size X of the detecting elements 30 in the two small X-ray detectors 9a and 9c that cover the local $FOV_L$ shown in FIG. 1, and the size Xa of the detecting elements 30a in a section for detecting data from the local $FOV_L$ on the large X-ray detector 9b that covers the wide $FOV_W$ are made small, and the detecting elements 30 and 30a are arranged in the X-ray detectors 9a, 9b, and 9c at a small pitch Pa, high time resolution and high spatial resolution with respect to data from the local $FOV_L$ can be obtained. In particular, when the sizes X and Xa and the pitches P and Pa of the detecting elements 30 and 30a in the X-ray detectors 9a, 9b, and 9c for detecting data from the local $FOV_L$ are set to be equal, data processing can be facilitated.

Further, setting the size Xb of the detecting elements 30b in the section for detecting data from the outside of the local $FOV_L$ on the large X-ray detector 9b that covers the wide $FOV_W$ to one for detecting data necessary for at least image reconstruction and arranging the detecting elements 30b at the pitch Pb necessary for at least image reconstruction make it possible to simplify the structure of the X-ray detector 9b.

Figure 8:
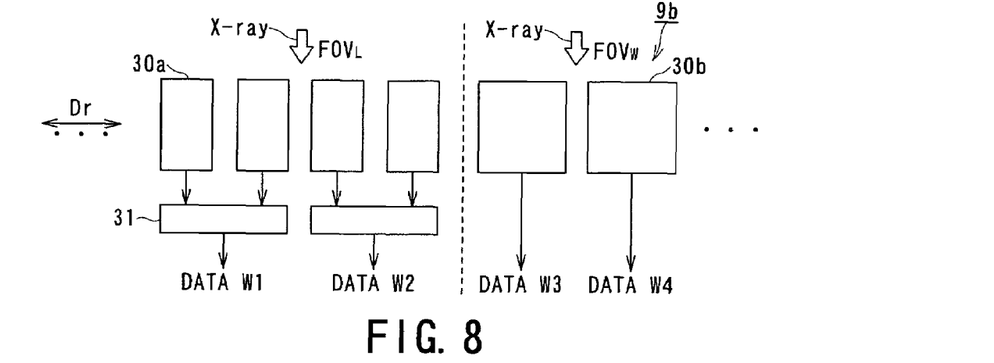
FIG. 8 is a diagram explaining the method for detecting data in case of acquiring the data from the wide $FOV_W$ using the X-ray detector shown in FIG. 7.
Figure 9:
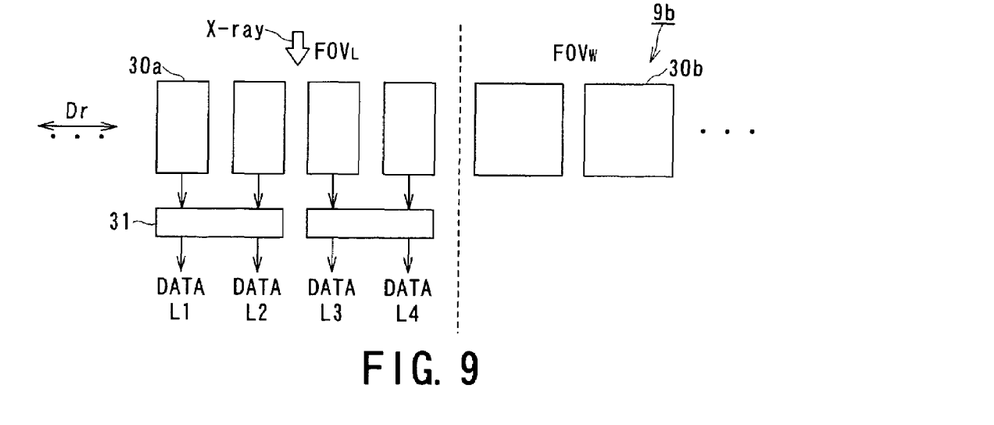
FIG. 9 is a diagram explaining the method for detecting data in case of acquiring the data from the local $FOV_L$ using the X-ray detector shown in FIG. 7.

FIG. 8 is a diagram explaining the method for detecting data in case of acquiring the data from the wide $FOV_W$ using the X-ray detector 9b shown in FIG. 7. FIG. 9 is a diagram explaining the method for detecting data in case of acquiring the data from the local $FOV_L$ using the X-ray detector 9b shown in FIG. 7.

When data is acquired from the wide $FOV_W$ with the X-ray detector 9b, X-rays are detected by both the detecting elements 30a having the small size and the small pitch and the detecting elements 30b having the large size and the large pitch on the X-ray detector 9b. Therefore, when charges accumulated in the detecting elements 30a and 30b are used as detection data without change, the time resolution and spatial resolution are not uniform among the detection data. Accordingly, signal distributing and combining circuits 31 are provided on output sides of the detecting elements 30a having the small size, as shown in FIG. 8.

In case of acquiring data from the wide $FOV_W$, signals outputted from a fixed number of (two in FIG. 8) detecting elements 30a are combined to output as single detection data (DATA W1, DATA W2) by each of the signal distributing and combining circuits 31. Consequently, more uniform detection data (DATA W1, DATA W2, DATA W3, DATA W4) can be acquired.

In contrast, in case of acquiring data from the local $FOV_L$ with the X-ray detector 9b, X-rays are detected only by the detecting elements 30a having the small size X, as shown in FIG. 9. Signals outputted from the detecting elements 30a having the small size X are outputted as detection data (DATA L1, DATA L2, DATA L3, DATA L4) by the signal distributing and combining circuits 31. This can achieve higher spatial resolution and higher time resolution.

In the X-ray CT apparatus 1A shown in FIG. 7, the X-ray detectors 9a, 9b, and 9c may have the same size, and one or both of the size and pitch of the detecting elements in any of the X-ray detectors 9a, 9b, and 9c may be changed in order to increase the time resolution and spatial resolution with respect to data from a local FOV.

What is claimed is:

1. An X-ray CT apparatus comprising:
   three X-ray generating units arranged so as to make an angle formed by a first X-ray exposure direction and a second X-ray exposure direction on a rotational plane thereof be a same angle as that formed by the second X-ray exposure direction and a third X-ray exposure direction on the rotational plane, the same angle being smaller than 120 degrees;
   three groups of detecting elements arranged opposite to the three X-ray generating units respectively so as to make a field of view formed in a center wider than two side fields of view; and
   a reconstructing unit configured to reconstruct an image using detection data detected by at least desired one of the three groups of the detecting elements,
   wherein the reconstructing unit is configured to switch a first mode for using data from a local region for half reconstruction and a second mode for using data from a region wider than the local region for full reconstruction, the data from the local region being obtained by using the three groups, the data from the region wider than the local region being obtained by using a center one of the three groups.

2. An X-ray CT apparatus according to claim 1, wherein the three groups are arranged in individual X-ray detectors respectively.

3. An X-ray CT apparatus according to claim 1, further comprising a supporting member supporting at least two of the three groups of the detecting elements in common.

4. An X-ray CT apparatus according to claim 1, further comprising a scan control unit configured to perform scanning with switching a first imaging mode for acquiring data of a local region using the three groups of the detecting elements and a second imaging mode for acquiring data of a region wider than the local region using a center one of the three groups.

5. An X-ray CT apparatus according to claim 1, further comprising a scan control unit configured to perform scanning in an imaging mode for acquiring data by outputting energies which are different across the three groups respectively.

6. An X-ray CT apparatus according to claim 1, further comprising a scan control unit configured to perform scanning in an imaging mode for acquiring data by outputting energies which are different between two groups of said three groups, a center one of the three groups not being one of the two groups.

7. An X-ray CT apparatus according to claim 1, wherein the reconstructing unit is configured to use data from a local region for half reconstruction, the data from the local region being obtained by using the three groups, further comprising an absorption correction unit configured to perform an absorption correction of image data using data on outside of the local region and on a region wider than the local region obtained by a center one of the three groups, the image data being obtained by half reconstructing processing of the reconstructing unit.

8. An X-ray CT apparatus comprising:
   three X-ray generating units arranged so as to expose X-rays in mutually different rotational radius directions and make angles formed by adjacent two X-ray exposure directions mutually unequal;
   three groups of detecting elements arranged opposite to the three X-ray generating units respectively so as to make a field of view formed in a center wider than two side fields of view;
   a supporting member supporting at least two of the three groups in common; and
   a reconstructing unit configured to reconstruct an image using detection data from at least desired one of the three groups,
   wherein the reconstructing unit is configured to switch a first mode for using data from a local region for half reconstruction and a second mode for using data from a region wider than the local region for full reconstruction, the data from the local region being obtained by using the three groups, the data from the region wider than the local region being obtained by using a center one of the three groups.

9. An X-ray CT apparatus according to claim 8, wherein the three groups are configured to form fields of views of which some are wider than remaining ones.

10. An X-ray CT apparatus according to claim 8, wherein the supporting member is formed as a cast integrated with a rotational frame supporting the three X-ray generating units and the three groups.

11. A data detecting method of X-ray CT apparatus, comprising steps of:
    exposing an X-ray from at least one of three X-ray generating units arranged in positions so as to make an angle formed by a first X-ray exposure direction and a second X-ray exposure direction on a rotational plane thereof be a same angle as that formed by the second X-ray exposure direction and a third X-ray exposure direction on the rotational plane, the same angle being smaller than 120 degrees;
    detecting an exposed X-ray as detection data using at least one of three groups of detecting elements arranged opposite to the three X-ray generating units respectively so as to make a field of view formed in a center wider than two side fields of view; and
    reconstructing an image using the detection data, wherein a first mode for using data from a local region obtained by using the three groups for half reconstruction and a second mode for using data from a region wider than the local region for full reconstruction are able to be switched, the data from the region wider than the local region being obtained by using a center one of the three groups.

12. A data detecting method of X-ray CT apparatus according to claim 11,
wherein the three groups are arranged on individual X-ray detectors respectively.

13. A data detecting method of X-ray CT apparatus according to claim 11,
wherein at least two of the three groups are supported by a supporting member in common.

14. A data detecting method of X-ray CT apparatus according to claim 11,
wherein scanning is performed with switching a first imaging mode for acquiring data of a local region using the three groups of the detecting elements and a second imaging mode for acquiring data of a region wider than the local region using a center one of the three groups.

15. A data detecting method of X-ray CT apparatus according to claim 11,
wherein scanning is performed in an imaging mode for acquiring data by outputting energies which are different across the three groups respectively.

16. A data detecting method of X-ray CT apparatus according to claim 11,
wherein scanning is performed in an imaging mode for acquiring data by outputting energies which are different between two groups of said three groups, a center one of the three groups not being one of the two groups.

17. A data detecting method of X-ray CT apparatus according to claim 11,
wherein data from a local region obtained by using the three groups is used for half reconstruction, further comprising a step of performing an absorption correction of image data using data on outside of the local region and on a region wider than the local region obtained by a center one of the three groups, the image data being obtained by half reconstructing processing.

18. A data detecting method of X-ray CT apparatus, comprising steps of:
exposing an X-ray from at least one of three X-ray generating units arranged so as to expose X-rays in mutually different rotational radius directions and make angles formed by adjacent two X-ray exposure directions mutually unequal;
detecting an exposed X-ray as detection data by at least one of three groups of detecting elements arranged opposite to the three X-ray generating units respectively so as to make a field of view formed in a center wider than two side fields of view, at least two of the three groups being supported by a common supporting member; and
reconstructing an image using the detection data,
wherein a first mode for using data from a local region obtained by using the three groups for half reconstruction and a second mode for using data from a region wider than the local region for full reconstruction are able to be switched, the data from the region wider than the local region being obtained by using a center one of the three groups.

19. A data detecting method of X-ray CT apparatus according to claim 18,
wherein the three groups form fields of view of which some are wider than remaining ones.

20. A data detecting method of X-ray CT apparatus according to claim 18,
wherein the common supporting member is formed as a cast integrated with a rotational frame supporting the three X-ray generating units and the three groups.

* * * * *